United States Patent [19]

Bixler

[11] Patent Number: 5,707,347
[45] Date of Patent: Jan. 13, 1998

[54] IMPACT-DISPERSING KNEE BRACE

[76] Inventor: Dickie Ray Bixler, Rte. 1, Box 33, Dacoma, Okla. 73731

[21] Appl. No.: 645,730

[22] Filed: May 14, 1996

[51] Int. Cl.[6] ............................................. A61F 5/00
[52] U.S. Cl. ............................................. 602/26; 602/16
[58] Field of Search ............................. 602/5, 6, 12, 16, 602/20, 23, 26

[56] References Cited

U.S. PATENT DOCUMENTS

| | | |
|---|---|---|
| 4,183,099 | 1/1980 | Lacey . |
| 4,624,247 | 11/1986 | Ford . |
| 4,791,916 | 12/1988 | Paez . |
| 4,872,448 | 10/1989 | Johnson, Jr. . |
| 4,986,264 | 1/1991 | Miller . |
| 5,018,514 | 5/1991 | Grood et al. ............... 602/26 X |
| 5,384,913 | 1/1995 | Hendry ..................... 602/26 X |
| 5,476,442 | 12/1995 | Madej . |

*Primary Examiner*—Linda C. Dvorak

[57] ABSTRACT

An impact-dispersing knee brace consisting of an inner frame or skeleton and an outer protective shell. Both are affixed to side supports with the supports being hinged to provide flexibility to the knee. The double wall construction helps disperse impact forces, especially side impact forces, throughout the device. The outer shell also protects the knee-cap and back of the knee when the knee is extended and prevents the leg from hyperextending. A spring-biased hinge mechanism allows for slight movement and give in the device.

7 Claims, 3 Drawing Sheets

IMPACT-DISPERSING KNEE BRACE

BACKGROUND OF THE INVENTION

1. Technical Field

The present invention relates generally to orthopedic devices, and, more specifically, to an impact-dispersing knee brace for stabilizing and protecting the knee of an athlete during contact sporting events.

2. Background

During many sporting activities, the knee is susceptible to receive unusually strong forces or impacts. This may cause a twisting or hyperextension of the knee joint which can lead to ligament sprains or tears in the meniscus, the protective cartilage covering the surfaces of the femur and tibia. Fractures, dislocations and other injuries, such as bleeding into the joint, known as hemarthrosis, and inflammation of the joint lining (synovitis) may result from a single sharp blow to the knee or from repetitive stressful knee actions. Particularly troublesome are side impacts to the knee, which often result in a strain or tear of the lateral or medial collateral ligaments.

Certain knee protection apparatuses and knee braces have been heretofore proposed, such as U.S. Pat. Nos. 4,183,099; 4,624,247; 4,791,916; 4,872,448; 4,986,264; and 5,476,442. None of these devices, however, appear to perform the dual function of stabilizing the knee joint during strenuous activity while also effectively dispersing impact forces directed to the knee, especially side impacts, such as is the object of the present invention.

SUMMARY OF THE INVENTION

The present invention is an impact-dispersing knee brace consisting of an inner frame or skeleton and an outer protective shell. Both the inner frame and the outer shell are affixed to side supports, with the supports being hinged to provide flexibility for the knee. The "double wall" construction helps disperse impact forces, especially side impact forces, throughout the device. The force of a blow to the side of the knee is distributed throughout the outer shell of the device and is dissipated around both sides of the knee. The outer shell also protects the knee-cap from direct frontal and rear blows when the leg is extended and functions to prevent the leg from hyperextending. A spring-biased hinge mechanism allows for slight movement and give in the device to aid in impact dispersion and increase comfort. A gap between the inner frame and outer protective shell also allows the outer shell to flex in response to impact forces.

More specifically, the impact-dispersing knee brace comprises an upper cuff for placement around the lower thigh just above the knee and a lower cuff for placement around the lower leg just below the knee. Both the upper and lower cuffs each comprise an arcuate anterior segment hinged to a similarly arcuate posterior segment. Both the anterior and posterior segments have an arcuate inner frame or skeleton, in the form of two straps or bands. The inner frame elements are affixed to and extend between an inner portion of two complementary side frame members and abut the surface of the leg. An arcuate outer shell is affixed to and extends between an outer portion of the side frame members such as to form an impact-dispersing protective covering. The upper cuff and lower cuff are rotatably connected so that the knee retains full flexibility during use. The significant components of the invention are made of a resilient plastic, such that the device is relatively small and lightweight.

In accordance with one aspect of the invention an adjustable hinge is used to connect the anterior and posterior segments of the upper and lower cuffs. The adjustable hinge allows degree of separation between the anterior segments and the posterior segments to be altered. Consequently, the present invention is universal insofar as its dimension can be adjusted to account for various leg sizes.

In accordance with another aspect of the invention, a hook and loop fastener, such as VELCRO, or other fastening means is used to fasten the unhinged side of the anterior segments to the unhinged side of the posterior segments. Thus, the user can quickly and easily don or doff the device.

In accordance with another aspect of the invention, two pair of jointed side support arms are used to rotatably connect the upper cuff and the lower cuff. Each of the side support arms is spring-biased and coaxially engaged within a side frame member. A jointed pair of arms is used on each side of the device, with one arm being coaxially engaged within a side frame member of the upper cuff posterior segment and the other being coaxially engaged within a corresponding side frame member of the lower cuff posterior segment. This spring-biased hinge mechanism allows for a slight axial movement of the upper cuff away from the lower cuff and provides the device with some give which increases performance and comfort.

In accordance with a further aspect of the invention, the anterior outer shell of the upper cuff is provided with a downwardly extending lip while the anterior outer shell of the lower cuff has a complementary upwardly extending lip. When the leg is straightened or extended the lips will abut or meet, thus preventing hyperextension of the leg. The lips also prevent a helmet or other piece of equipment from directly contacting vulnerable areas, such as the knee-cap.

In accordance with another aspect of the invention, the posterior outer shell of the upper cuff has a cut-away lower region corresponding to a similar area on the posterior outer shell of the lower cuff. These cut-away regions allow for a normal, full flexion of the leg during use.

A better understanding of the invention and its objects and advantages will become apparent to those skilled in this art from the following detailed description, taken in conjunction with the attached drawings, wherein there is shown and described only the preferred embodiment of the invention, simply by way of illustration of the best mode contemplated for carrying out the invention. As will be realized, the invention is capable of modifications in various obvious respects, all without departing from the invention. Accordingly, the description should be regarded as illustrative in nature and not as restrictive.

DETAILED DESCRIPTION OF THE PREFERRED EMBODIMENT

Figure 1:
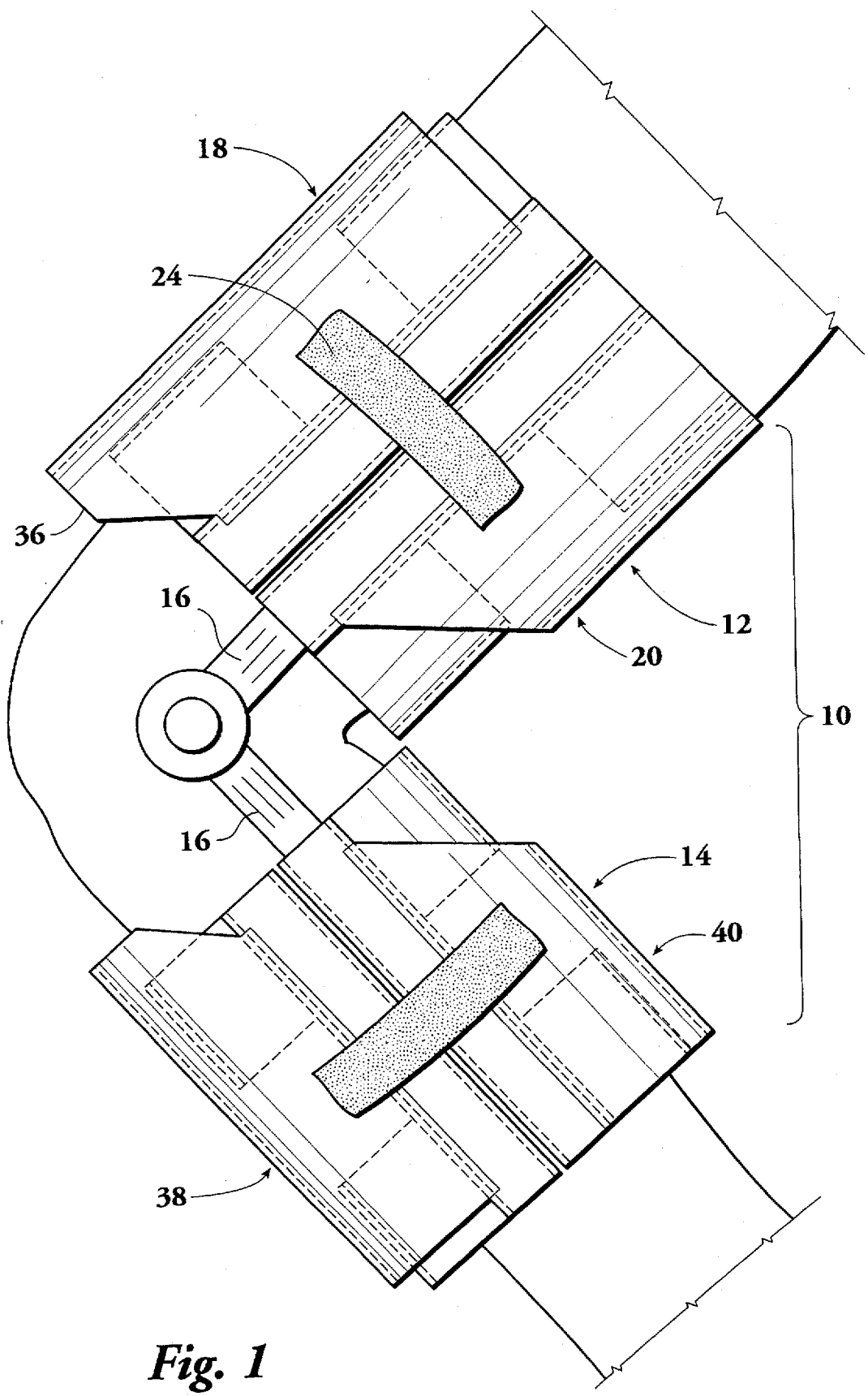
FIG. 1 is a side-elevational view of the preferred embodiment in its operative position affixed about the knee.

Referring initially to FIG. 1, the preferred embodiment is shown in its operative position. The impact-dispersing knee brace, generally indicated by the reference number 10, is comprised of an upper cuff 12 and a lower cuff 14. The upper cuff 12 is fastened around the lower thigh at a point slightly above the knee. The lower cuff 14 is placed around an upper portion of the lower leg. Both the upper cuff 12 and the lower cuff 14 entirely circumscribe the front and back of the thigh and lower leg respectively. Two pair of jointed side support arms 16 serve to rotatably connect the upper cuff 12 and the lower cuff 14 on the lateral and medial sides of the device.

Referring now to FIGS. 2–6 in addition to FIG. 1, the upper cuff 12 will be examined in more detail. It should be understood, however, that the ensuing description pertaining to the upper cuff 12 is equally applicable to lower cuff 14, as the lower cuff 14 is essentially the mirror image of the upper cuff 12.

Figure 3:
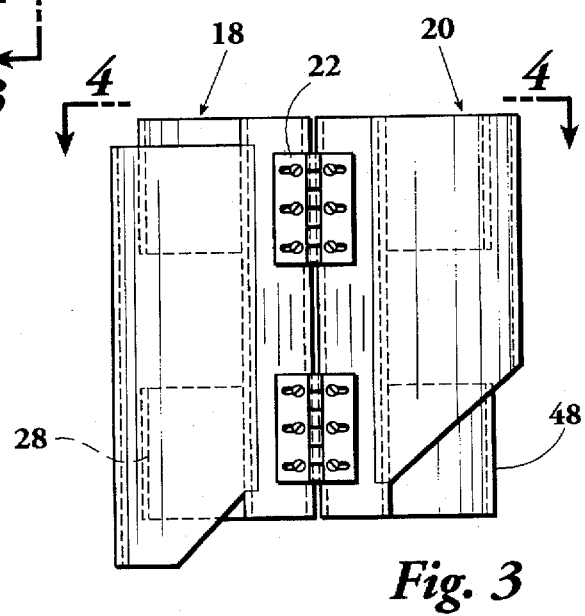
FIG. 3 is a side-elevational view taken along line 3—3 of FIG. 2.

The upper cuff 12 is bisected into two arcuate segments. An arcuate anterior segment 18 is hinged to a similarly arcuate posterior segment 20 to form the upper cuff 12. FIG. 3 shows an adjustable hinge 22 that may be used to connect the anterior segment 18 to the posterior segment 20. The adjustable hinge 22 allows the degree of separation between the anterior segment 18 and posterior segment 20 to be altered. This allows for the modification of the device to account for different leg dimensions. The adjustable hinge 22 is shown for illustrative purposes only, and it is recognized that a variety of alternate coupling means, including adjustable means, might be substituted therefore. A fastener, such as a hook and loop (VELCRO) fastener 24, is used to fasten the unhinged side of the anterior segment 18 to the unhinged side of the posterior segment 20 to provide for the fast and easy application and removal of the device.

Figure 4:
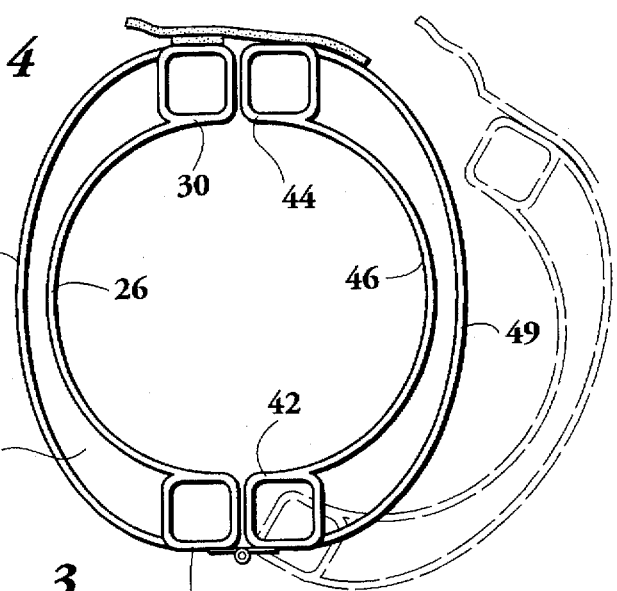
FIG. 4 is a top view taken along line 4—4 of FIG. 3.
Figure 2:
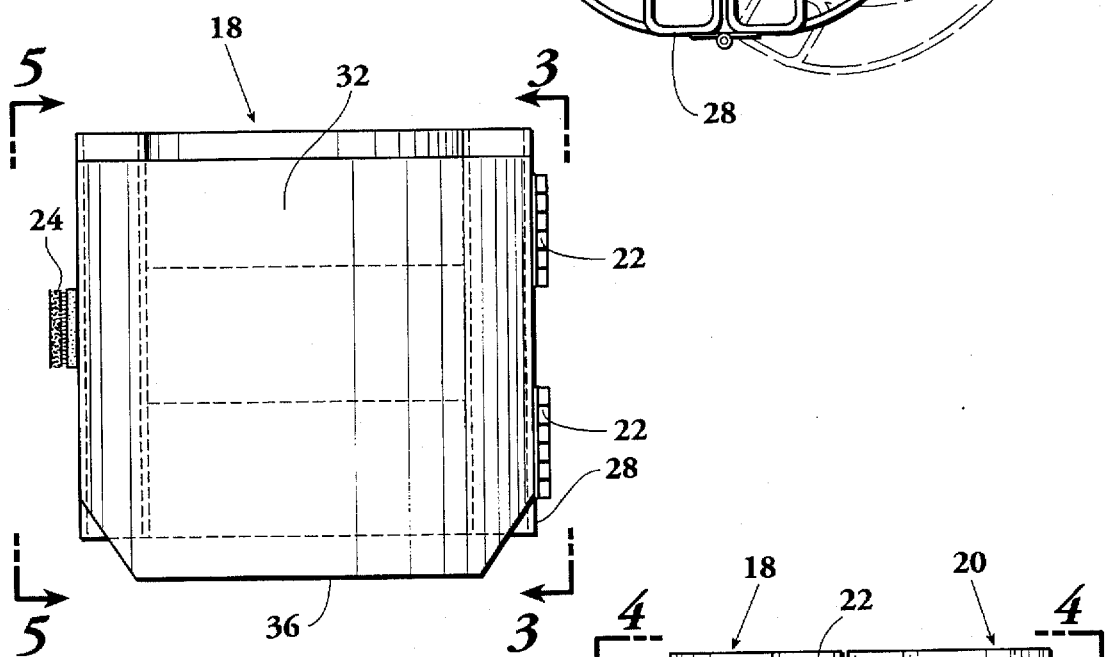
FIG. 2 is a front-elevational view of the preferred embodiment.

As best seen in FIG. 4, the anterior segment 18 and posterior segment 20 each include two side frame members which, when the device is in use, are aligned parallel to the longitudinal axis of the leg on the medial and lateral sides thereof. Focusing now on the arcuate anterior segment 18, there is an inner frame element 26 in the form of a band affixed to and extending between an inner portion of side frame members 28, 30. In the preferred embodiment two such inner frame elements are used to form a "skeleton" for placement adjacent to the surface of the leg. A second inner frame element 28 is shown hidden in the majority of views.

The inner frame elements 26, 28 together comprise an inner layer or wall of what is a dual-wall device. An arcuate outer shell or wall 32 is affixed to and extends between an outer portion of side frame members 28, 30 such as to overlay inner frame element 26. A space 34 exists between the inner frame element 26 and the outer shell 32. This space 34 allows the resilient outer shell 32 to slightly compress upon an impact to aid in impact dispersion. The outer shell 32 is provided at its lower end with a downwardly extending lip 36.

As shown in FIG. 1, the anterior segment 38 of the lower cuff 14 has the same construction as the anterior segment 18 of the upper cuff 12. In fact, when in its operative position, the anterior segment 38 of the lower cuff 14 is the mirror image of the anterior segment 18 of the upper cuff 12. Consequently, separate discussion of the construction of this anterior segment 38 is not necessary. Likewise, the construction of the posterior segment 20 of the upper cuff 12 is the same as that of the posterior segment 40 of the lower cuff 14.

Focusing now on the drawings in relation to the posterior segment 20, it includes two side frame members 42, 44 and arcuate inner frame elements 46, 48 in the form of straps or bands affixed to and extending between an inner portion of the side frame members 42, 44. The outer shell 49 that is affixed to and extends between the outer portion of the side frame members 42, 44 of the posterior segment 20 has a cut-away lower region to prevent the device from impeding full flexion of the leg. As the posterior segment 40 of the lower cuff 14 has a complementary cutout region, wearing the device does not limit the range of motion of the knee.

Figure 7:
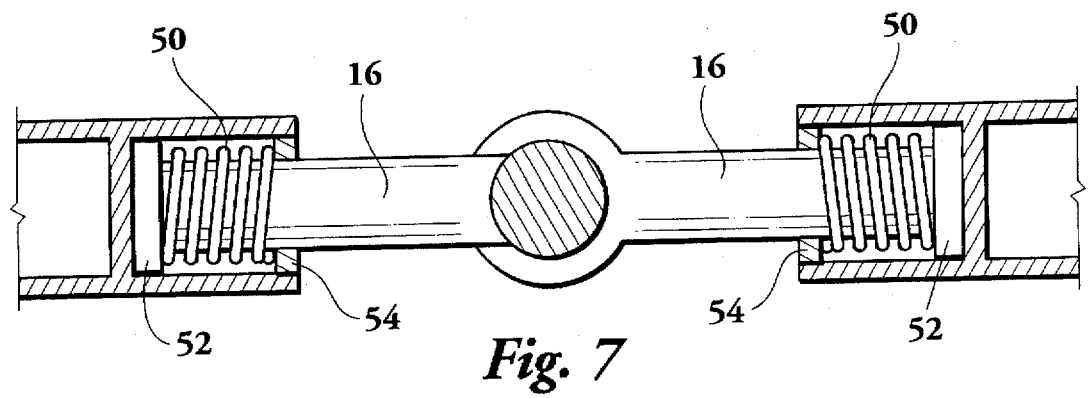
FIG. 7 is a cross-section of a pair of jointed side support arms for rotatably connecting the upper and lower cuffs.
Figure 6:
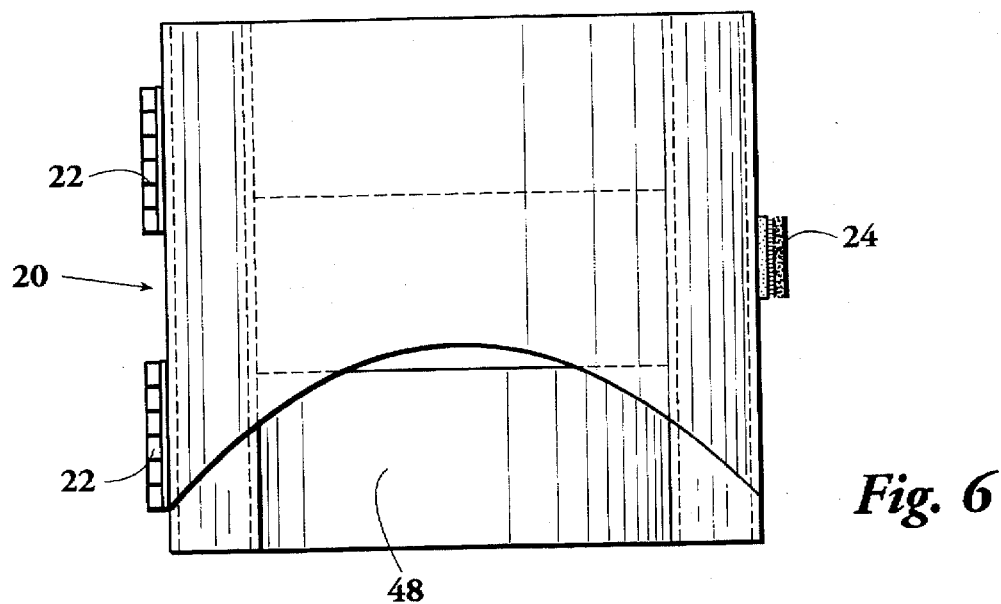
FIG. 6 is a rear-elevational view taken along line 6—6 of FIG. 5.
Figure 5:
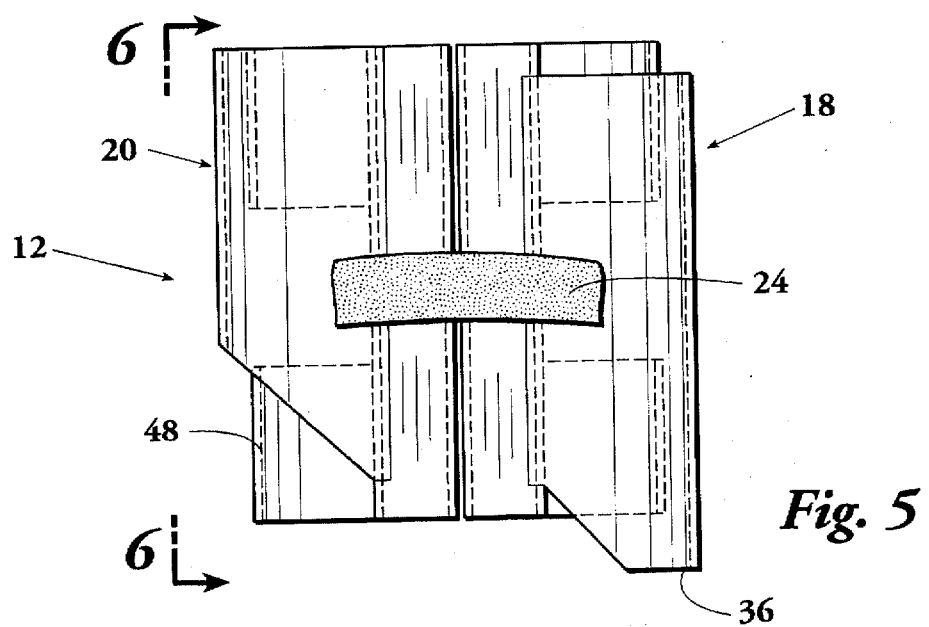
FIG. 5 is a side-elevational view taken along line 5—5 of FIG. 2.

The means for rotatably connecting the upper cuff 12 and the lower cuff 14 is variable, but a preferred means is illustrated. Two pair of jointed side support arms 16 are coaxially engaged within opposing side frame members as shown more particularly in FIG. 7. The side support arms 16 are hinged for rotation. A safety stop may be added to the hinge as additional protection against hyperextension of the knee joint. The side support arms 16 are spring-biased within the side frame members. With specific reference to FIG. 7, a spring 50 separates the head 52 of the side support arm 16 from a piston stop 54 located at the bottom of the side frame member. With this design, the upper cuff 12 and the lower cuff 14 may move slightly away from each other if required due to the position of the leg or due to receiving an angular blow.

It is to be understood that alternate means of rotatably connecting the upper cuff 12 and the lower cuff 14 may be utilized. In particular, the hinging means shown and described in U.S. Pat. Nos. 4,624,247; 4,791,916; and 4,986,264, which patents are incorporated herein by reference, could be used if desired.

The device, and especially the side frame members, inner frame elements, and outer shell are preferably constructed of a lightweight, resilient plastic material. The segments are preferably unitary components manufactured in any number of common methods known to those skilled in the art. Comfort may be enhanced by providing a thin cushion or lining on the underside of the inner frame members to abut the skin. A rubber or synthetic rubber lining is preferred.

In operation, the device is attached to the leg as described above either under a uniform or clothing or outside a pant leg, whichever is desired. The knee joint is stabilized by the supporting structure surrounding it. Impact forces directed to the knee are dispersed throughout the outer shell rather than being focused on one small area. The device is particularly adept in preventing damage to the lateral or medial collateral ligaments during a side impact. During such an impact, the impact force is transmitted throughout the device via the side supports and the outer protective shell. The impact force is thus dissipated around the entire circumference of the knee as opposed to being focused on the extremely vulnerable lateral or medial side of the knee. The lips of the anterior segments of the device function to protect the knee-cap from a direct blow in addition to preventing the hyperextension of the knee. The device is lightweight and easy to use. Owing to the cut-out regions on the posterior segments, the device does not impede the proper flexion of the knee, allowing the athlete to perform to optimum capability.

Whereas, the present invention has been described in relation to the drawings attached hereto, it should be understood that other and further modifications, apart from those shown or suggested herein, may be made within the spirit and scope of this invention.

What is claimed is:

1. An impact-dispersing knee brace, comprising:
   (a) an upper cuff for placement around the lower thigh and a lower cuff for placement around the lower leg, said upper and lower cuffs each comprising an arcuate anterior segment hinged to a similarly arcuate posterior segment, said anterior and posterior segments each having an arcuate inner frame element affixed to and extending between an inner portion of two complementary side frame members and an arcuate outer shell affixed to and extending between an outer portion of said side frame members; and (b) a hinge for connecting said upper cuff and said lower cuff.

2. The impact-dispersing knee brace according to claim 1, wherein said inner frame elements and said outer shells are made of a resilient plastic.

3. The impact-dispersing knee brace according to claim 1, further comprising an adjustable hinge for hinging said anterior segments and said posterior segments such that the degree of separation between said anterior segments and said posterior segments may be altered.

4. The impact-dispersing knee brace according to claim 1, further comprising a hook and loop fastener for fastening the unhinged side of said anterior segments to the unhinged side of said posterior segments.

5. The impact-dispersing knee brace according to claim 1, wherein said hinge for connecting said upper cuff and said lower cuff comprises two pair of jointed side support arms, one pair of said arms being located on the lateral side of said brace and the other pair of said arms being located on the medial side of said brace, one of said arms of each said pair being spring-biased and coaxially engaged within said side frame member of said upper cuff posterior segment and the other said arms of each said pair being spring-biased and coaxially engaged within said side frame member of said lower cuff posterior segment.

6. The impact-dispersing knee brace according to claim 1, wherein said anterior outer shell of said upper cuff has a downwardly extending lip and said anterior outer shell of said lower cuff has an upwardly extending lip such that when the leg is extended said lips meet, thus preventing hyperextension of the leg.

7. The impact-dispersing knee brace according to claim 1, wherein said posterior outer shell of said upper cuff has a cut-away lower region and said posterior outer shell of said lower cuff has a cut-away upper region such that said outer posterior shells will not contact despite full flexion of the leg.

* * * * *

UNITED STATES PATENT AND TRADEMARK OFFICE
CERTIFICATE OF CORRECTION

PATENT NO. : 5,707,347
DATED : January 13, 1998
INVENTOR(S) : Dickie Ray Bixler

It is certified that error appears in the above-identified patent and that said Letters Patent is hereby corrected as shown below:

Column 5, line 8 (claim 1), after "members" insert -- , and having an impact dispersing space between said inner frame element and said outer shell--.

Signed and Sealed this

Thirty-first Day of March, 1998

Attest:

BRUCE LEHMAN

Attesting Officer

Commissioner of Patents and Trademarks